(12) United States Patent
Olsen

(10) Patent No.: US 7,134,432 B2
(45) Date of Patent: Nov. 14, 2006

(54) INFANT BREATHING AID APPARATUS

(76) Inventor: Thomas Olsen, P.O. Box 3121, St. Francisville, LA (US) 70775

( * ) Notice: Subject to any disclaimer, the term of this patent is extended or adjusted under 35 U.S.C. 154(b) by 27 days.

(21) Appl. No.: 10/853,354

(22) Filed: May 25, 2004

(65) Prior Publication Data

US 2005/0263157 A1    Dec. 1, 2005

(51) Int. Cl.
  A61M 16/00  (2006.01)
  A62B 18/08  (2006.01)
  A61J 17/00  (2006.01)
(52) U.S. Cl. .......................... 128/200.26; 128/206.29; 606/234
(58) Field of Classification Search .......... 128/200.26, 128/203.12, 202.27, 200.15, 203.26, 203.27, 128/204.14, 206.21, 206.27, 206.29; 606/234, 606/235, 236
See application file for complete search history.

(56) References Cited

U.S. PATENT DOCUMENTS

| | | | |
|---|---|---|---|
| 4,520,809 A * | 6/1985 | de Greef et al. | 128/200.24 |
| 5,375,593 A * | 12/1994 | Press | 128/207.18 |
| 5,685,291 A | 11/1997 | Marsh | |
| 5,904,140 A | 5/1999 | McGoogan | |
| 6,470,882 B1 | 10/2002 | Newhouse et al. | |
| 6,526,966 B1 | 3/2003 | Peesay | |
| 6,557,548 B1 | 5/2003 | Dickson | |
| 6,626,168 B1 | 9/2003 | Carroll et al. | |
| 6,776,157 B1 * | 8/2004 | Williams et al. | 128/203.12 |
| 2002/0112724 A1 | 8/2002 | Newhouse et al. | |
| 2004/0040556 A1 | 3/2004 | Fillyaw | |

* cited by examiner

Primary Examiner—Teena Mitchell
(74) Attorney, Agent, or Firm—Keaty Professional Law Corporation

(57) ABSTRACT

A breathing aid for an infant is adapted for delivery of inhalable medication in a gentle flow to an area immediately adjacent the baby's nasal passageway. An oral member formed as a pacifier carries a hollow tube, the open top end of which extends just above the upper rim of the mouth guard of the pacifier. A swivel connector secured to the bottom of the tube allows easy adjustment of the position of the breathing aid in relation to the mouth guard and to a connecting hose, through which oxygen or other medication is delivered.

7 Claims, 2 Drawing Sheets

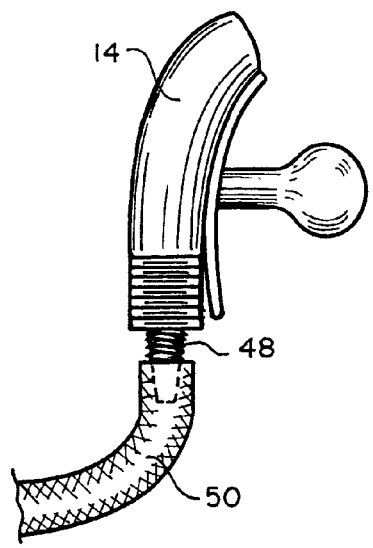
F I G. 4
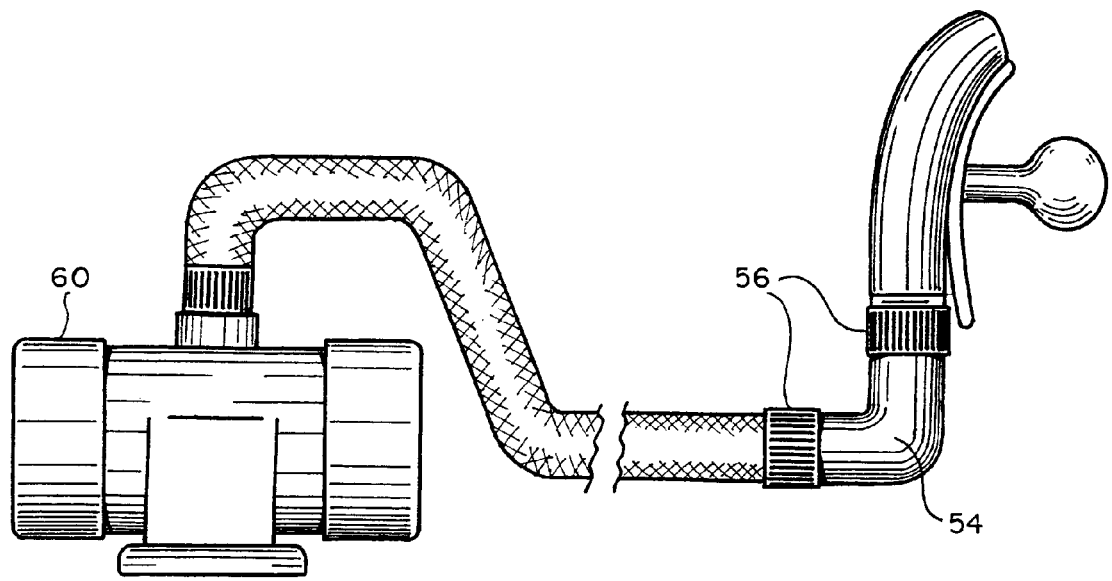
F I G. 5

INFANT BREATHING AID APPARATUS

BACKGROUND OF THE INVENTION

The present invention relates generally to devices for assisting the breathing of an infant suffering from respiratory problems, nasal congestion, and the like. More particularly, the present invention relates to an apparatus combined with a baby pacifier for inserting into the mouth of the infant for quieting the infant, while delivering oxygen or medication to the infant.

Delivery of a breathing aid medication is indicated in many instances when an infant suffers from cold, breathing disorders, has underdeveloped lungs, as is often the case with premature babies, and in a number of other instances when oxygen or medicated spray needs to be administered to a child. Conventional breathing aids, such as oxygen masks and the like present a problem when used with a baby. The babies tend to change their position frequently during sleep or during waking hours. A baby may also find the breathing mask uncomfortable and may become restless trying to take the mask off. It was noted that the infants tend to breath through their noses and therefore, delivery of a nasal decongestant, oxygen, or vaporized medication if delivered in front of the baby's nose, is likely to be breathed in by the infant.

Various solutions have been offered to the problem of delivering a breathable medication to the infant in combination with a pacifier, which the infant sucks. For instance, U.S. Pat. No. 6,526,966 discloses a nebulizer for infants which combines a feeding bottle attached to a gas delivery guide to permit the infant to bottle nurse while being nebulized. Another solution is offered in U.S. Pat. No. 6,557,548, where a vapor or an aromatic substance is administered to a child who has trouble breathing. The breathing aid assembly in accordance with the '548 patent, combines a pacifier with a vapor emitter which is insertable in a specially provided chamber of the pacifier nipple. A releasable cover attaches to the oral member, which resembles a nipple of a conventional pacifier.

Still another solution is offered by U.S. Pat. No. 6,626,168, where a nipple is combined with a nebulizing assembly having a mask, which is adaptable to cover the infant's nose and mouth and facilitate the delivery of an inhalable medication to infant and toddler.

While the above solutions may work under certain conditions, it is noted that the bulky construction of some of the known devices may present difficulty in retaining the devices in place when the baby is lying down, or is restless, or often changes his position.

The present invention contemplates elimination of drawbacks associated with the prior art and provision of an infant breathing aid that is compact and adapted for connection to an external gas supply, be it an oxygen source or a nebulizer.

SUMMARY OF THE INVENTION

It is, therefore, an object of the present invention to provide an infant breathing aid apparatus that can be easily attached and disconnected from a medication-supplying source.

It is another object of the present invention to provide an infant breathing aid apparatus, which can be used as a pacifier to quiet a child, while the medication or oxygen is delivered to adjacent nasal passageway of the infant.

It is a further object of the present invention to provide a breathing aid apparatus that easily adjusts to the position of the infant, while continuing to deliver inahlable medication.

These and other objects of the present invention are achieved through a provision of a breathing aid apparatus for an infant that comprises an oral member for placing into the mouth of an infant and a delivery member secured to an exterior surface of the oral member. The delivery member has a delivery end and is configured such that the delivery end extends below the nasal passageway of the infant.

The oral member has a nipple for placing into the baby's mouth and a mouth guard, which is shaped as an outwardly convex plate. The delivery member is a hollow body, which is carried by an exterior surface of the oral member and is bent to follow the curvature of the convex plate. The mouth guard has an upper wall provided with a depression, and the delivery end of the delivery member extends, at least in part, above the depression. The opening formed in the delivery end directs the inhalable medication into an area immediately adjacent to the baby's nose, allowing the baby to breath in the medication in a normal breathing cycle.

A lower portion of the delivery member carries a swivel fitting, which allows free rotation of the swivel member in relation to the main body of the delivery member. A securing fitting is secured to a free end of the swivel fitting, the free end being adapted for connection to a flexible hose, which delivers oxygen to the delivery end. In the alternative embodiment, a second swivel fitting is connected to the first swivel fitting through an intermediate connector. The connector may be elbow-shaped. The second swivel member may be connected to a larger diameter hose, which in turn is adapted for connection to a nebulizer.

BRIEF DESCRIPTION OF THE DRAWINGS

Reference will now be made to the drawings, wherein like parts are designated by like numerals, wherein

FIG. 4 is a schematic view illustrating connection of the infant breathing aid apparatus of the present invention to an oxygen-supplying hose.

FIG. 5 is a schematic view illustrating the use of the infant breathing aid apparatus of the present invention with a second swivel fitting connected to a nebulizer.

DETAILED DESCRIPTION OF THE PREFERRED EMBODIMENT

Figure 1:
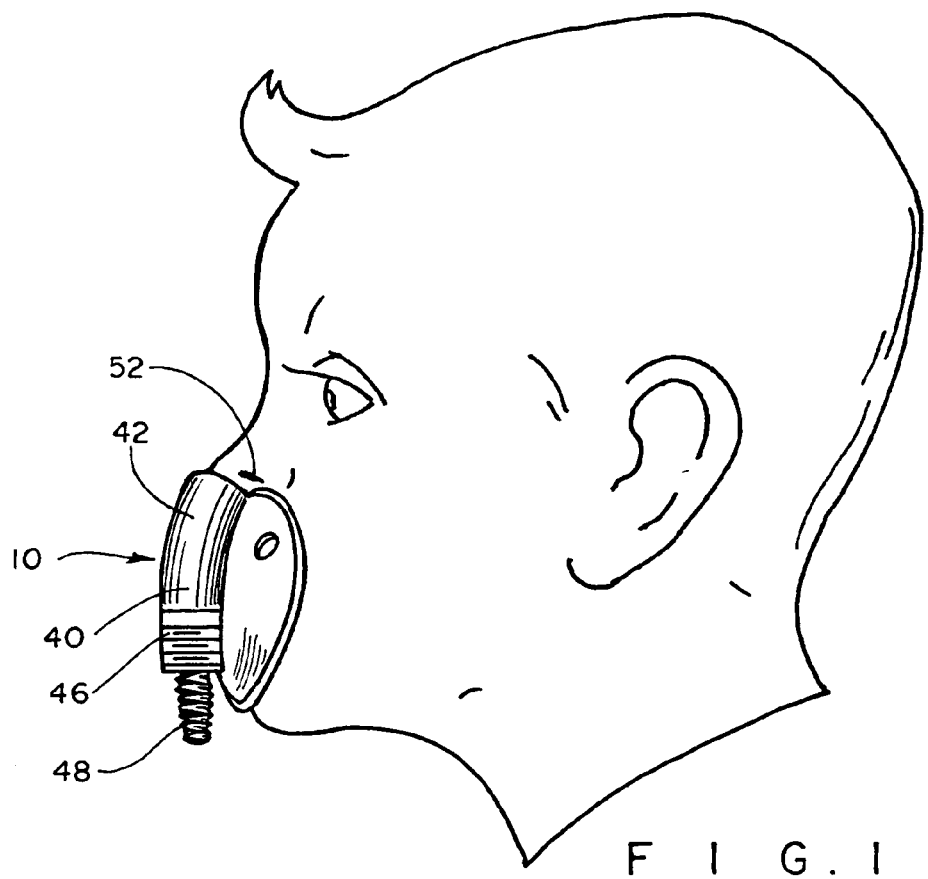
FIG. 1 is a perspective view of the infant breathing aid apparatus in accordance with the present invention.
Figure 2:
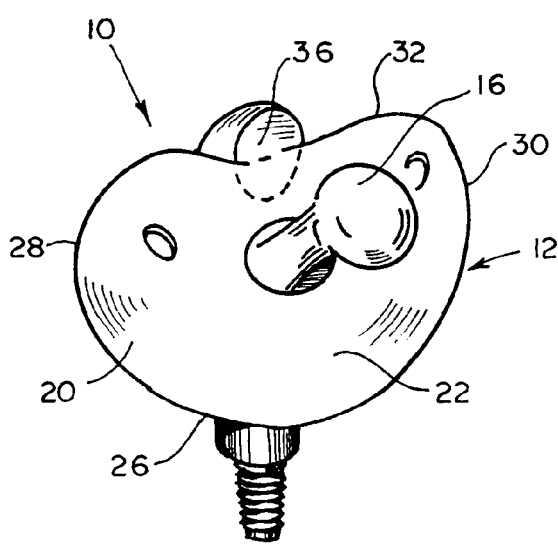
FIG. 2 is a perspective view of the infant breathing device of the present invention showing a delivery member secured to an exterior surface of a mouth guard.

Turning now to the drawings in more detail, numeral 10 designates the infant breathing aid apparatus in accordance with the present invention. As can be seen in the drawings, the device 10 comprises an oral member 12 and a delivery member 14. The oral member 12 is formed as a pacifier, comprising a nipple 16 and a mouth guard 20. The nipple 16 is preferably molded from non-toxic flexible resilient material, such as latex, rubber, and the like. The mouth guard 20 is formed from a non-toxic rigid or semi-rigid plastic, such as polypropylene, nylon, and the like.

The mouth guard 20 is outwardly convex, it is contoured to fit over a mouth of an infant and terminate below the nasal passageway of the baby. The mouth guard 20 has an inner surface 22 and an exterior surface 24, which are generally smooth and protrusion free. The mouth guard 20 is defined by a bottom wall 26, opposing side walls 28 and 30, and an upper wall 32. The walls 28 and 30 are mirror images of each other and extend to a distance sufficient to prevent an infant from taking the pacifier portion (oral portion) entirely into his mouth. The upper wall 32 of the mouth guard 20 has an arcuate depression 34, which dips slightly downwardly towards the center of the mouth guard 20. The depression 34 ensures that the nasal passageway of the infant is not blocked by the solid mouth guard.

Figure 3:
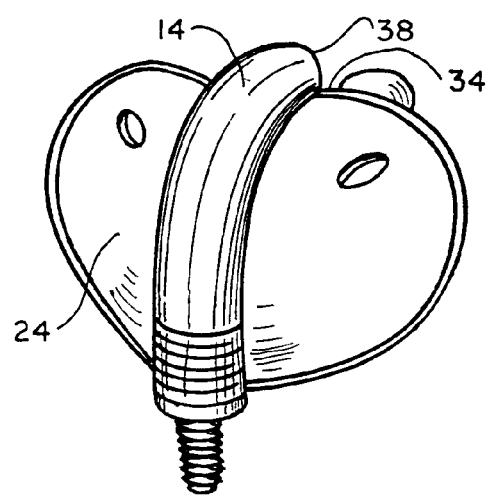
FIG. 3 is a perspective view of the infant breathing aid apparatus of the present invention in operation, with the pacifier placed in a baby's mouth.

The delivery member 14 is formed as a hollow conduit having a delivery end with an opening 36, at least a portion of which extends above the upper wall 32 in the area where the depression 34 is formed. The opening 36 may be partially closed by the mouth guard 20 (FIG. 1) or may be entirely open with the delivery end extending above the depression 34 (FIG. 3).

The delivery member 14 is configured as a curved tube 40 with an upper part 42, which turns inwardly towards the nipple 16, and a bottom portion 44, which extends substantially downwardly, following the configuration of the exterior surface 24 of the mouth guard 20. The delivery member 14 has longitudinal dimension substantially equal or slightly greater than the vertical dimension of the mouth guard 20.

The present invention provides for a means for adjusting position of the delivery member relative to a medication delivery hose and to the mouth guard. In the embodiment, where the apparatus 10 is designed for use with an oxygen supply source, at least one such adjusting means is provided. The adjusting means comprises a fitting 46, which is detachably secured in a free rotational relationship to the lower portion 44 of the tube 40. The swivel fitting 46 rotates about a central axis of the tube 40.

Secured to a free end of the swivel fitting 46 is a securing fitting 48 adapted for engagement with an oxygen-supplying hose 50. As shown in FIG. 4, the securing fitting 48 is be engaged with the flexible hose 50, which supplies oxygen to the delivery opening 36 through hollow fittings 48, 46 and the tube 40. In the case of a nebulizer use and a delivery hose 52 of a larger diameter than the hose 50, the present invention provides for the use of a second adjusting means 56 detachably connected through an elbow connector 54 to the first swivel fitting 46. The second swivel fitting 56, similarly to the fitting 46, allows free rotation of the hose 52, easily adjusting to the position of an infant. The hose 52 allows securing the delivery member 14 to a nebulizer 60.

In operation, an infant caregiver places the pacifier 12 in the baby's mouth, allowing the baby to suck on the nipple 16. The opening 36 extends just below the nose of the infant, allowing delivery of oxygen or other inhalable medication through the tube 40. The baby may be sitting, laying in bed, she can move his head sideways and still the medication or the oxygen will be delivered in a gentle flow to an area just below the baby's nostrils.

The swivel fittings 46 and 56 allow the tube 40 to easily adjust its position following the movement of the infant without creating an inconvenient restriction for the baby. Since there are no bulky devices and the delivery member does not exceed the size of the pacifier 12, the baby is not alarmed by connection of her pacifier to the source of inhalable medication. The infant breathes in the oxygen with the medication in a natural breathing cycle, while sucking on the nipple 16.

The device 10 is lightweight, compact and can be adjusted for use with an oxygen source or with an nebulizer by substituting the securing fitting 48 with the second swivel fitting 56. The apparatus 10 can be injection-molded as a single piece, with the swivel fittings 46 and 56 being detachable and easily substitutable for adapting the device 10 for use with oxygen supply apparatus or with a nebulizer.

Many changes and modifications may be made in the design of the present invention without departing from the spirit thereof. I therefore pray that my rights to the present invention be limited only by the scope of the appended claims.

I claim:

1. An infant breathing aid apparatus, comprising:

an oral member for placing in the mouth of an infant and a nasal delivery member secured to an exterior surface of the oral member, said delivery member being configured and sized such that a dispensing end of the delivery member is positioned below a nasal passageway of the infant, wherein a lower end of the delivery member carries a means for adjusting position of said lower end in relation to the oral member.

2. The apparatus of claim 1, wherein said adjusting means comprises at least one swivel fitting detachably secured on said lower end for a free rotation about a vertical axis of the delivery member.

3. The apparatus of claim 2, wherein said at least one swivel fitting carries a securing fitting for connecting said delivery member to an external source of inhalable medication.

4. The apparatus of claim 1, further comprising a second adjusting means detachably secured to said at least one adjusting means through an intermediate connecting member to facilitate adjusting position of the second adjusting means to the oral member.

5. The apparatus of claim 4, wherein said second adjusting means comprises a swivel fitting adapted for connecting said delivery member to an external source of inhalable medication.

6. An infant breathing aid apparatus, comprising:

an oral member for placing in the mouth of an infant and a nasal delivery member secured to an exterior surface of the oral member, said delivery member comprising a hollow tube having an upper dispensing end and a lower end, said delivery member being configured and sized such that a dispensing end of the delivery member is positioned immediately adjacent a nasal passageway of the infant, and wherein the delivery member is sized to not substantially exceed the size of the oral member, wherein said connecting means comprises at least one swivel fitting detachably secured to the lower end of the hollow tube and a securing fitting to allow attachment of the delivery member to a conduit delivering the inhalable medication.

7. An infant breathing aid apparatus, comprising:

an oral member for placing in the mouth of an infant and a nasal delivery member secured to an exterior surface of the oral member, said delivery member comprising a hollow tube having an upper dispensing end and a lower end, said delivery member being configured and sized such that a dispensing end of the delivery member is positioned immediately adjacent a nasal passageway of the infant, and wherein the delivery member is sized to not substantially exceed the size of the oral member, wherein said connecting means comprises a first swivel fitting detachably secured to the lower end of the hollow tube and a second swivel fitting detachably connected to the first swivel fitting through a connecting member, said first swivel fitting and said second swivel fitting being adapted for free rotation to facilitate adjustment in the position of the delivery member in relation to the conduit delivering inhalable medication.

* * * * *